United States Patent [19]
Krogh et al.

[11] Patent Number: 5,443,077
[45] Date of Patent: Aug. 22, 1995

[54] METHOD OF MONITORING THE POSITION OF A SENSOR

[75] Inventors: Soren-Christian Krogh, Måløv; Erik Aksbro, Rødovre, both of Denmark

[73] Assignee: Radiometer A/S, Copenhagen, Denmark

[21] Appl. No.: 90,156

[22] PCT Filed: Jan. 21, 1992

[86] PCT No.: PCT/DK92/00014
§ 371 Date: Jul. 23, 1993
§ 102(e) Date: Jul. 23, 1993

[87] PCT Pub. No.: WO92/12670
PCT Pub. Date: Aug. 6, 1992

[30] Foreign Application Priority Data
Jan. 23, 1991 [DK] Denmark .................. 0108/91

[51] Int. Cl.$^6$ .............................. A61B 5/06
[52] U.S. Cl. .................... 128/737; 128/897
[58] Field of Search .......... 128/653.1, 897–899, 128/772, 207.014, 207.015, 737, 630

[56] References Cited

U.S. PATENT DOCUMENTS 4,416,289 11/1983 Bresler .
4,526,177 7/1985 Rudy et al. .
4,905,698 3/1990 Strohl, Jr. et al. .
4,943,770 7/1990 Ashley-Rollman et al. .

FOREIGN PATENT DOCUMENTS 0320623 6/1989 European Pat. Off. .
WO90/01160 2/1990 WIPO .

OTHER PUBLICATIONS

PCT International Search Report for PCT Application No. PCT/DK92/00014.

Primary Examiner—William E. Kamm
Assistant Examiner—John P. Lacyk
Attorney, Agent, or Firm—David M. Klein; Bryan Cave

[57] ABSTRACT

When performing the method a sensor (1) is used with a coil (15) integrated in a coil circuit. In the coil circuit a magnetic field is generated so that mutual induction can develop between the coil circuit and the surroundings of the sensor (1). The magnetic field in the coil circuit is detected intermittently, and a developed mutual induction is detected as a change of the magnetic field. The position of the sensor is monitored on the basis of said intermittent detection of the magnetic field in the coil circuit. The change of the magnetic field in the coil circuit can be detected in several ways. If the magnetic field is varying, the change may for example be detected as a change of the peak value of the voltage across or the current intensity through the coil circuit or be detected as a phase shift of one of these parameters. The method is used especially to ensure that calibration of the sensor (1) is performed only when the sensor (1) is located in a related calibration chamber (24). The detectable mutual induction is developed between the coil circuit with the coil (15) and an aluminum cup (22) constituting the calibration chamber (24).

18 Claims, 6 Drawing Sheets

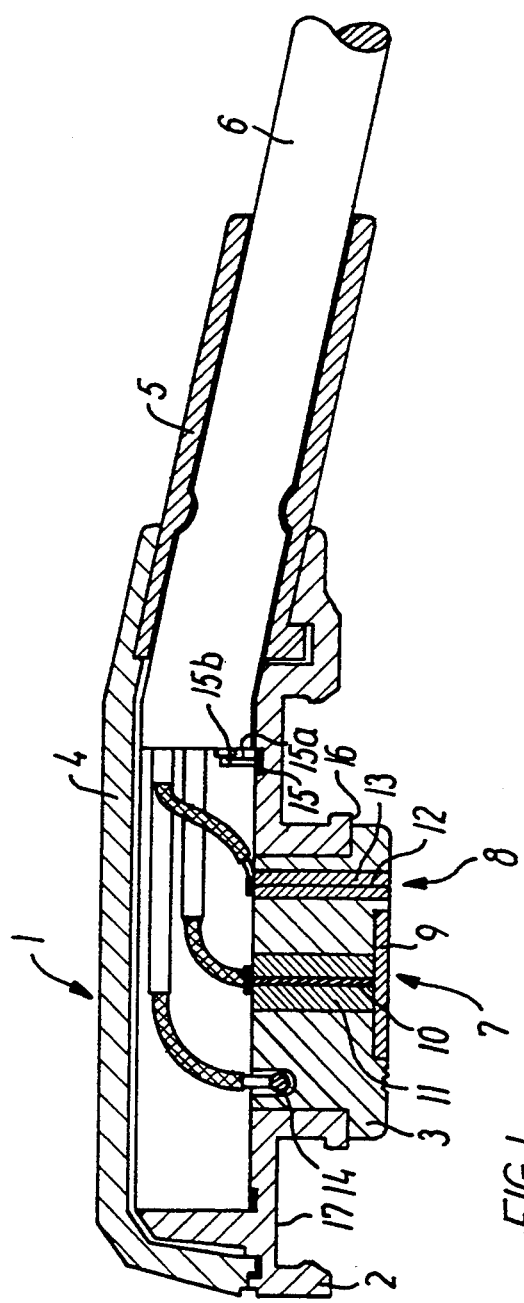
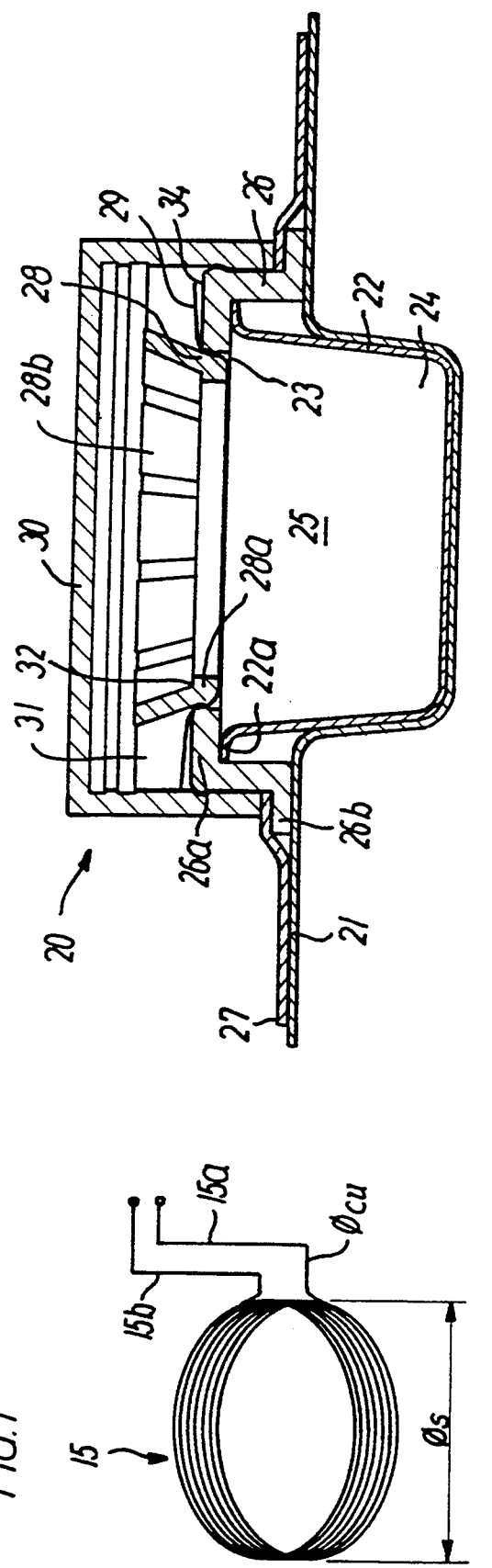

METHOD OF MONITORING THE POSITION OF A SENSOR

BACKGROUND OF THE INVENTION

1. Field of the Invention

The present invention relates to a method of monitoring the position of a sensor.

2. Description of the Related Art

Sensors for measuring the presence of one or several components in a fluid have been known for several decades. The components may be for example ions or in the form of gas and be present in various fluids. The sensors may be based on various measuring principles, for example electrochemical measuring principles such as potentiometry, amperometry and polarography, and optical measuring principles.

It is common to most of the sensors that at a time during use they must be located in a certain position, and it may be of crucial importance that the sensor is located correctly. To ensure this, many systems are provided with position detectors. The determination of the position may be to detect whether the sensor is located correctly in a measuring chamber, as for example in measuring devices wherein a replaceable sensor is located in a combined measuring and calibration chamber built into a monitor. The determination may also simply comprise detection of where in the system the sensor is, as for example in measuring devices for in vivo measurements where the sensor during measuring is in direct contact with a patient and during calibration is located in a separate calibration chamber. To ensure that the sensor is not calibrated when located on a patient, it may be necessary automatically to check whether the sensor is present in the calibration chamber when calibration is activated.

An example of such measuring device is the monitor of the type TCM3 from Radiometer A/S, Copenhagen, Denmark. Said monitor is adapted for transcutaneous (tc) measuring of the $O_2$ and/or $CO_2$ content in blood. Calibration of a sensor in the form of an electrode connected to the monitor is performed with the electrode located in a calibration chamber placed in the monitor itself to which the calibration gas is supplied through a tube assembly from a separate calibration device.

To ensure that calibration of the electrode is not performed while the electrode is located on a patient, a micro switch is built into the calibration chamber, detecting whether the electrode is located in the chamber. Thus, activation of the calibration is only possible when the micro switch detects that the electrode is in position in the chamber.

Apart from controlling the possibility of calibration, the information from the micro switch may be used to control several other functions in the monitor as well. With the electrode located in the calibration chamber, the heat supply to the electrode is shut off after 30 minutes in the chamber, ensuring that the electrolyte between the electrode and the membrane does not evaporate disproportionately quickly when the electrode is not used. Moreover, other functions—necessary only when measuring—are disconnected, for example the acoustic alarm is suppressed and the curve printout and the data sampling by a connected recorder are stopped.

The TCM3 monitor itself is a compact portable unit, but the relating calibration device, which has a volume corresponding to half the volume of the monitor (24×8×23 cm), makes the entire unit quite unwieldy.

In order to provide a measuring system which is easy to carry, a new type of calibration device has been developed with much smaller dimensions (approx. 4×1×4 cm). Said calibration device is disclosed in applicant's patent application PCT/DK89/00092, publication no. WO 90/01160. The calibration device is a mass-produced disposable device and comprises primarily a base foil into which a completely closed calibration cup is pressed, containing the fluid for calibration of a sensor.

When a sensor is to be calibrated, it is inserted into the calibration device whereby the cover of the calibration cup is ruptured, the sensor penetrates into the cup and is brought in contact with the calibration fluid.

With the newly-developed calibration device the advantage is obtained that when calibrating the electrode mentioned above need not be placed in a calibration chamber on the monitor, but calibration can be performed in close proximity to the patient. For example, on in vivo monitoring of neonates the electrode need not be removed from the incubator during calibration, as the calibration device is so small that it can easily be placed inside the incubator.

However, the calibration device does not render it possible to use the micro switch mentioned in connection with the TCM3 monitor to detect whether the electrode is present in the calibration chamber, as no electronic parts exist in the separate calibration device. To build a micro switch into the electrode is not a good solution to the problem; firstly it will make the electrode large and unwieldy and secondly the risk of the micro switch being activated by other than the calibration device is too big. In addition, the gel required in order to establish a good contact between the electrode and the skin of a patient is likely to contaminate the micro switch, causing failures and faulty detections.

However, it is very important to ensure, especially with the newly-developed calibration device by which it is possible to calibrate the electrode while located inside the incubator, that calibration is not performed while the electrode is located on a patient, but only when the electrode is located in the calibration chamber.

SUMMARY OF THE INVENTION

Therefore, the object of the invention is to provide a method for a safe monitoring of the position of a sensor. This is obtained by the method according to the invention which is characteristic in that a sensor is used comprising a coil integrated in a coil circuit, wherein a magnetic field is generated; that the coil is constructed and arranged in the sensor in such a way that the magnetic field produced in the coil circuit extends beyond the delimitations of the sensor; that the magnetic field in the coil circuit is intermittently detected; that mutual induction between the coil circuit and the surroundings of the sensor is detected as a change of the magnetic field in the coil circuit; and that the position of the sensor is monitored on the basis of the intermittent detection of the magnetic field in the coil circuit.

The magnetic field in the coil circuit of the sensor may be generated by applying an alternating voltage across the coil circuit or making an alternating current flow through the circuit. The extension of the magnetic field depends on the magnitude of the applied voltage or current. As the sensor is put near an object which is influenced by the magnetic field, a counteracting magnetic field will be produced in that object, the magnitude of which i.a. is dependent on the distance between the sensor and the object. The resulting developed mutual induction between the coil circuit and the object outside the sensor will change the magnetic field in the coil circuit. When the magnetic field in the coil circuit changes, the alternating voltage across and the alternating current through the coil circuit as well as the phase of each of these change. Thus, it is possible to detect a change of the magnetic field in the coil circuit by intermittently measuring the peak value of the voltage or the current or the phase of one of these. A change of the magnetic field may also be detected by measuring parameters derived from those mentioned. It is only necessary to measure one of these parameters. In this context, intermittently means continuously or at different, possibly predetermined times.

In a first embodiment according to the invention the method comprises that for a given measurement parameter, the signal ranges, which represent given positions of the sensor, are predetermined. At a given time, the position of the sensor is then determined by comparing the signal for the magnetic field in the coil circuit detected at said given time with the predetermined signal ranges.

In another embodiment according to the invention, the quantity and the sign of the difference between signal values relating to given positions of the sensor are predetermined for a given measurement parameter. A change of position of the sensor between two given positions is then detected by the occurrence of a change in the detected signal for the magnetic field in the coil circuit, said change being larger than or equal to the predetermined quantity and having the related sign.

BRIEF DESCRIPTION OF THE DRAWINGS

The invention is further described below with reference to the drawing wherein

FIG. 1 is a partially sectional view of an electrode to be used by the method according to the invention, FIG. 1a is a schematic view of a detector coil used in the electrode shown in FIG. 1, FIG. 2 is a sectional view of a calibration device relating to the electrode shown in FIG. 1.

DESCRIPTION OF THE PREFERRED EMBODIMENT

Figure 3:
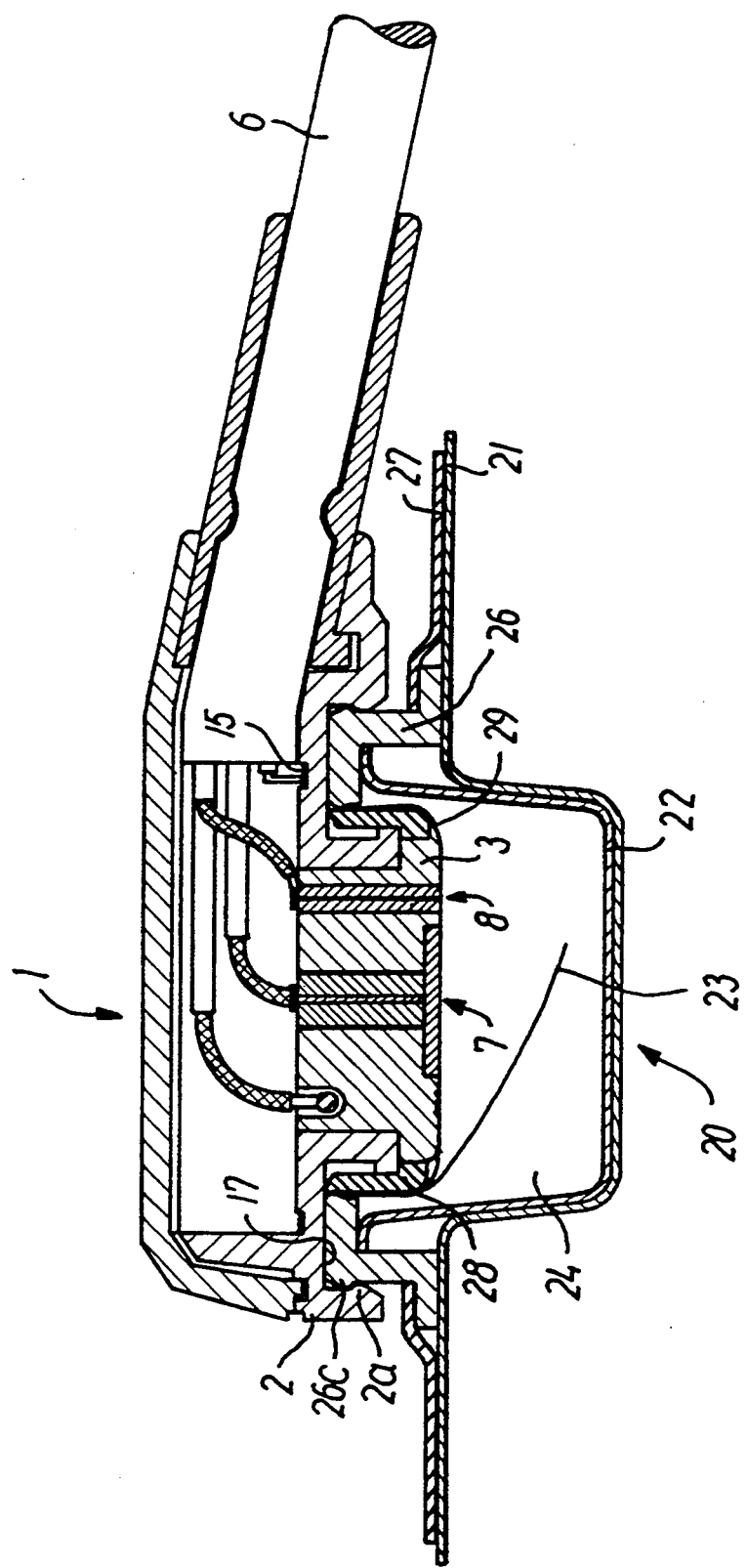
FIG. 3 is a partially sectional view of the electrode shown in FIG. 1 inserted into the calibration device shown in FIG. 2.

The embodiment shown in FIG. 1 of an electrode to be used by the method according to the invention comprises a combined electrode 1 for transcutaneous (tc) measuring of $pCO_2$ and $pO_2$. The electrode is constructed primarily in the same manner as existing well-known tc electrodes, for example the combined tc electrode of the type E5280 from Radiometer A/S, Copenhagen, Denmark. The electrode 1 comprises an electrode housing 2 into which an electrode body 3 of silver is glued. The electrode housing 2 is closed by a protection cap 4. The electrode 1 is by means of a cable 6 connected to a monitor (not shown), which controls the functions relating to in vivo monitoring, i.a. switch on/switch off of current circuits, processing of data, etc. The transition between the electrode 1 and the cable 6 is strengthened by a flexible bush 5.

In the electrode body 3, the sensor parts 7 and 8 for measuring of $pCO_2$ and $pO_2$ are located. The sensor parts 7 and 8 are located in such a manner that their measuring surfaces end on the outwards extending surface of the silver body 3. Measuring of $pCO_2$ is based on measuring of pH. The $pCO_2$ sensor part 7 comprises a solid state element 9 and a conductive wire 10, which connects the solid state element 9 with the cable 6. The solid state element 9 is constructed of several layers. The outer layer is a pH sensitive glass layer arranged on a layer of conductive glass which again is arranged on an intermediate conductor of Pt. All of this is carried by an insulating, ceramic basis. The conductive glass layer converts the measurement signal from the pH sensitive glass into electric signals and transmits said signals through the intermediate conductor to the conductive wire 10, which is surrounded by an insulating plastic tube 11 at the center of the silver body 3. The $pO_2$ sensor part 8 comprises a Pt wire 12 embedded in a glass element 13. The Pt wire 12 is connected with the cable 6 in the electrode housing 2. The electrode body 3 further comprises a heating element 14 in the form of a zener diode for heating of the electrode and the skin on which measurement is to be performed and a heat sensor (not shown) in the form of an NTC resistor. The heating element 14 as well as the heat sensor are by means of the cable 6 connected with the controlling monitor. In addition to forming a basis for the sensor parts 7 and 8, the heating element 14, etc., the silver body 3 of the electrode 1 also serves as a reference electrode and for that purpose it is chlorinated on its surface facing the electrode front. The silver body 3 is also by means of the cable 6 connected with the monitor.

In addition to the well-known elements mentioned above in connection with tc electrodes, the electrode housing 2 further comprises a coil 15, located in an annular groove along the outer edges of the interior of the electrode housing 2. The coil 15, which is shown schematically in FIG. 1a, consists of an enamel-insulated Cu wire with a diameter $\phi_{Cu}=0.05$ mm wound with 55 turns across a mandrel with a diameter $\phi_d=10.8$ mm. The coil with an inner diameter $\phi_s=\phi_d=10.8$ mm, is supplied by Oticon A/S, Copenhagen, Denmark, and has a resistance of 20 $\Omega$ and an inductance of 110 $\mu$H. The coil 15 is at its ends 15a and 15b connected to the cable 6. The function of the coil 15 will be explained further in connection with FIGS. 7, 8 and 9.

A sectional view of a calibration device 20 adapted to the electrode 1 is shown in FIG. 2, primarily comprising a calibration chamber, a membraning device, and a fixation means. The calibration device 20 consists of a silicone-coated base foil 21 into which is pressed and glued a foil cup 22 of aluminum, the edge of which ends in an outwards extending flange 22a. A cover 23, of aluminum foil too, is welded onto the flange 22a and closes the cup 22 tightly so that no exchange of matter will take place between a fluid contained in the chamber 24 delimited by said parts and the surroundings. The chamber 24 serves as a calibration chamber and contains a calibration fluid 25 with a well-known composition suitable for calibration of the electrode 1, the content of $O_2$ and $CO_2$ differing from the content of these components in the air. The calibration fluid may consist of for example 15% $O_2$, 5% $CO_2$ and the remainder $N_2$. The cup 22 is at its upper part, which is not attached to the base foil 21, surrounded by a fixation ring 26 consisting of a smooth tube section with two circular flanges located at each end of the tube section, the upper flange 26a of which extends inwardly and the lower flange 26b extends outwards. The lower flange 26b abuts on the base foil 21 and the upper flange 26a abuts on the flange 22a of the cup 22 and the cover 23. A fixation plaster 27 consisting of a gel adhesive with a mesh reinforcement is attached to the lower flange 26b of the fixation ring 26. The fixation plaster 27 is adapted to hold the fixation ring 26 against a not necessarily plane surface, for example the base foil 21, human skin, etc.

A squeezing ring 28, consisting of an annular ring 28a with upwards extending tabs 28b located along the outside edge which are elastically displaceable in radial direction, is located over the cover 23 within the flange 26a, so that the ring 28a engages with the flange 26a. Along the bottom of the squeezing ring 28 and held between this and the fixation ring 26, a 15 μm PP membrane 29 of the type which is usually used in tc electrodes for measuring of $pO_2$ and $pCO_2$ is located. The calibration device 20 is closed by a protection cap 30. At the bottom of the spacing 31, which is delimited by the fixation ring 26 and the protection cap 30, is located an bicarbonate-containing electrolyte.

When the tc electrode 1 shown in FIG. 1 is to be calibrated this is performed as follows:

First, any used membrane, etc. must be removed so that the electrode looks like the one shown in FIG. 1. The protection cap 30 on the calibration device 20 is removed and the electrode 1 is inserted into the calibration device 20 while attempting to center the silver body 3 of the electrode 1 in relation to the squeezing ring 28 in the calibration device 20. When the electrode 1 is pressed into the calibration device 20, the electrode front will press against the aluminum cover 23, which at a time will be ruptured and bend into the calibration chamber 24. Hereby some of the electrolyte fluid from the chamber 31 will flow into the chamber 24 and wet the calibration fluid contained herein. The remainder of the electrolyte fluid is locked up between the electrode body 3 and the membrane 29. By pressing the electrode 1 further into the calibration device 20, the projecting parts 16 of the electrode housing 2 will abut on the surface 32 of the circular ring 28a, and the squeezing ring 28 will be pressed downwardly in relation to the fixation ring 26. Hereby the tabs 28b will be pressed inwardly against the part of the electrode housing 2 surrounding the electrode body 3. When the electrode 1 is pressed completely into the calibration device 20 (see FIG. 3), the top surface 34 of the flange 26a of the fixation ring 26 abuts on the downward surface 17 of the electrode housing 2, a projecting part 2a of the electrode housing 2 is fixedly engaged with a projecting part 26c of the fixation ring 26, and the squeezing ring 28 is wedged between the fixation ring 26 and the electrode 1. The membrane 29 is stretched across the electrode front and held between the squeezing ring 28 and the fixation ring 26. The two parts, the electrode 1 and the calibration device 20, are now locked together and the electrode 1 is ready for calibration. The electrode 1 may, if desired, remain in the calibration chamber 24 after calibration, whereby the risk of the electrode 1 drying out is reduced while kept at ready mode.

Figure 4:
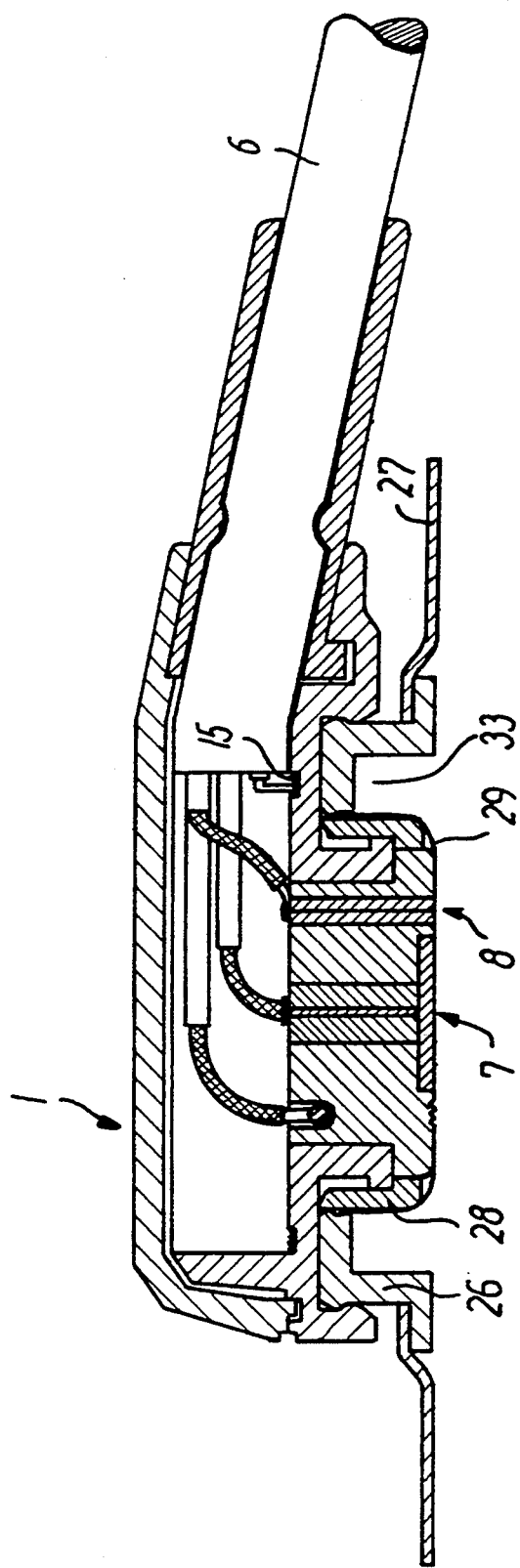
FIG. 4 is a partially sectional view of the electrode shown in FIG. 1 engaged with a fixation means for fastening the electrode to a patient.

After calibration the electrode 1 can be lifted out of the calibration chamber 24. This is done by lifting the fixation plaster 27 from the base foil 21 as the electrode 1 as mentioned above is in fixed engagement with the fixation ring 26 which is connected with the plaster 27. FIG. 4 shows a sectional view of the calibrated and membranated electrode 1 with a mounted fixation means after the electrode 1 is released from the calibration chamber 24. The electrode front with the measuring electrodes 7 and 8 may now be applied a dose of contact gel and then placed at the desired measuring site on the patient. The fastening to the skin of a patient is carried out by means of the fixation plaster 27 only.

Figure 5:
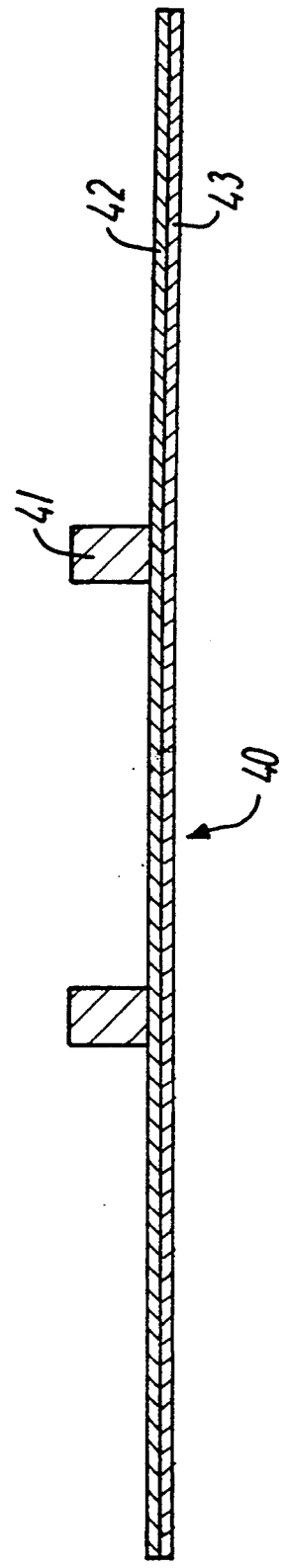
FIG. 5 is a sectional view of a parking means relating to the electrode shown in FIG. 1.
Figure 6:
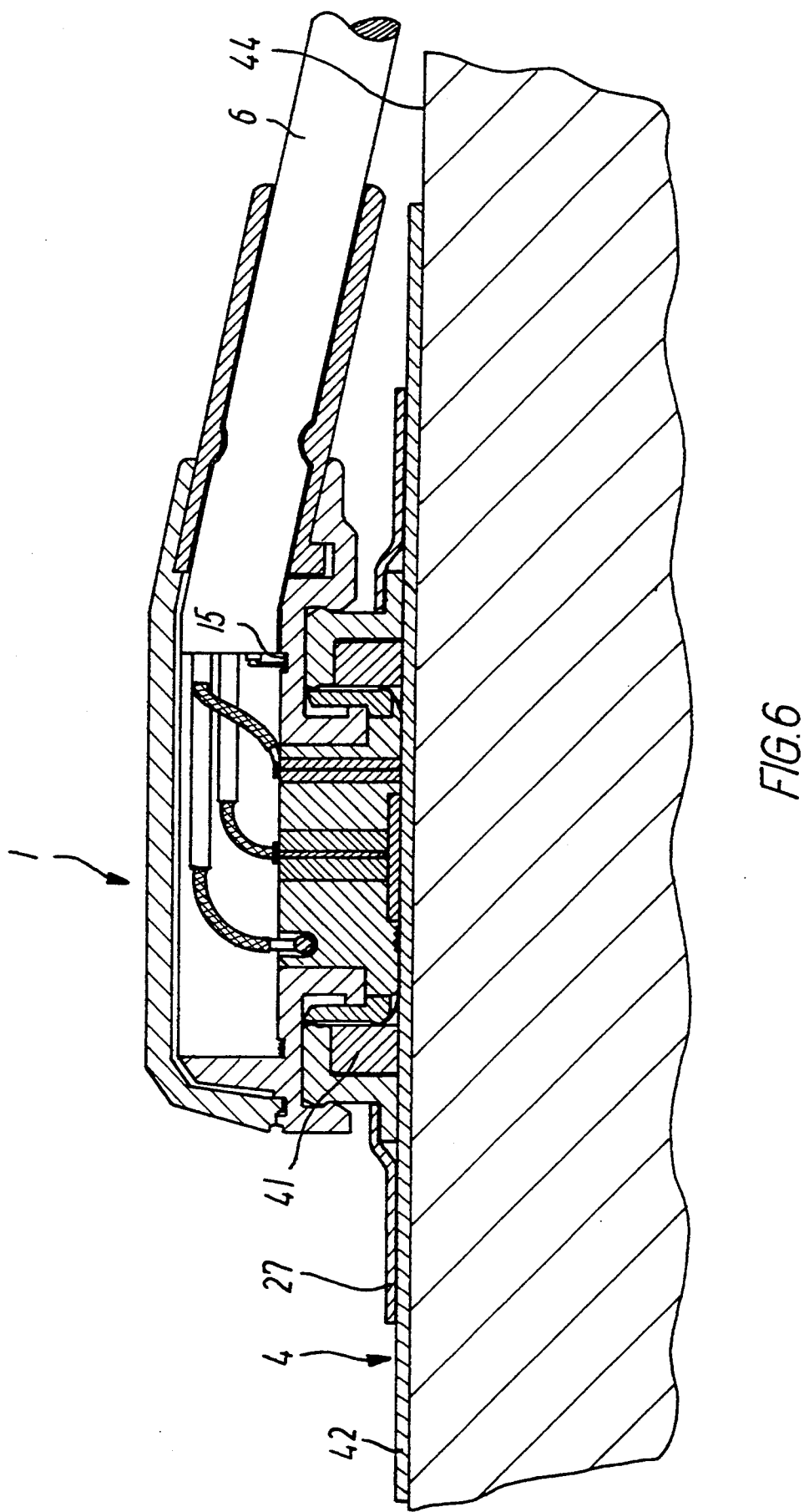
FIG. 6 is a partially sectional view of the electrode shown in FIG. 1 inserted into the parking means shown in FIG. 5 after it is placed on an arbitrary surface.

If desired, the electrode 1 may be kept (parked) in a special parking means 40 shown in FIG. 5. The parking means 40 consists of a metal ring 41, for example of aluminum, fixedly mounted on one side of a piece of silicone-treated plastic foil 42. The side of the foil 2 opposite the ring 41 is adhesive and on delivery protected by another, easily removable piece of foil 43. The ring 41 is adapted to the annular groove 33, which is delimited by the elements located at the electrode 1, the fixation ring 26, and the squeezing ring 28. After removal of the protection foil 43, the parking means 40 may be placed where desired. Moreover, it is possible to establish parking means several places so that the electrode 1 can be easily removed from the patient, if necessary, and parked so that it will not be in the way. FIG. 6 shows the electrode 1 parked in a parking means 40 which after removal of the protection foil 43 is located on a surface 44, for example on a wall in an incubator.

When the electrode 1 is to be calibrated again, the used membrane 29, the squeezing ring 28, and the fixation ring 26 are removed by stripping off the fixation ring 26 from its engagement with the electrode housing 2 whereafter the membrane 29, the squeezing ring 28 and the fixation ring 26 are discarded. The electrode 1 is now ready for recalibration.

Before using the electrode 1 shown on the drawing, including calibration and measuring, the electrode 1 is by means of the cable 6 connected to a monitor (not shown) which i.a. is a control unit for all the functions relating to calibration and measuring. When measuring, the monitor controls for example thermostating of the electrode 1 by means of the heating element 14 and the heat sensor, collection and printout of measurement data as well as some control functions, which activate the alarm function when measurement or control values are beyond the specified ranges. These functions are all known from former monitors for existing tc electrodes, for example the monitor mentioned above of the type TCM3 from Radiometer A/S, Copenhagen, Denmark. This monitor comprises a micro switch built into the calibration chamber which detects whether the electrode is positioned in the chamber. A similar function is obtained by the electrode 1 according to the invention by using the coil 15 mentioned in connection with FIG. 1.

When the electrode 1 is connected to a monitor, a sinusoidal alternating voltage U with a peak value $U_{peak}$ 1 V and a frequency $f_u$ 150 kHz is applied to the coil circuit.

As a result of the applied alternating voltage U, a magnetic field will develop in and around the coil circuit. When the electrode 1 is inserted into the calibration device 20, the aluminum cup 22 is influenced by the magnetic field from the coil circuit. The aluminum cup 22 will act as a short-circuited turn, and an electromotive force will be induced into this which will attempt to counteract the applied field. The counteracting field will again influence the coil circuit, and the voltage across this will be changed. In other words, a mutual induction develops between the coil circuit and the aluminum cup 22. Thus, the value for the peak value of the voltage across the coil circuit will decrease, and the phase of the measured voltage will be displaced in relation to the phase of the applied voltage. How much the magnetic field of the coil circuit influences the cup 22 and vice versa (how large the degree of coupling is between the coil circuit and the aluminum cup 22) is dependent on the distance between the coil 15 and the cup 22.

Figure 7:
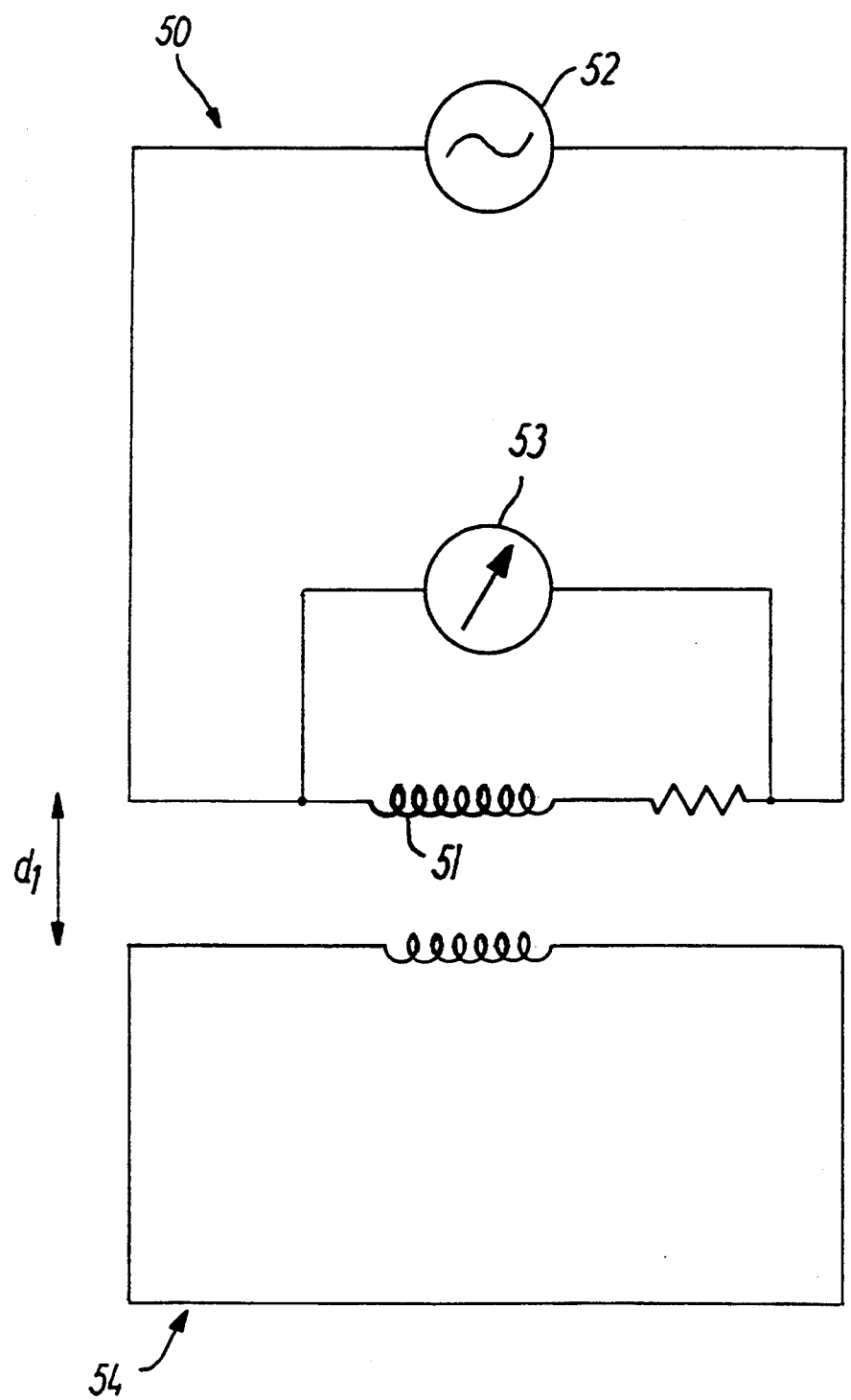
FIG. 7 is a circuit diagram, illustrating the interaction between the detector coil and the calibration cup.

The circuit diagram in FIG. 7, comprising two circuits 50 and 54 shows the above-mentioned system. The upper circuit 50 corresponds to the coil circuit in the electrode 1 with a coil 51 corresponding to the coil 15. Across the coil circuit 50, an alternating voltage is applied from a supply point 52, and the voltage across the coil circuit is measured by an AC voltmeter 53. The lower circuit 54 represents the aluminum cup 22, which acts as a short-circuit. The distance $d_1$ between the two circuits is variable, corresponding to the distance between the electrode 1 and the calibration device 22 being variable.

Figure 8:
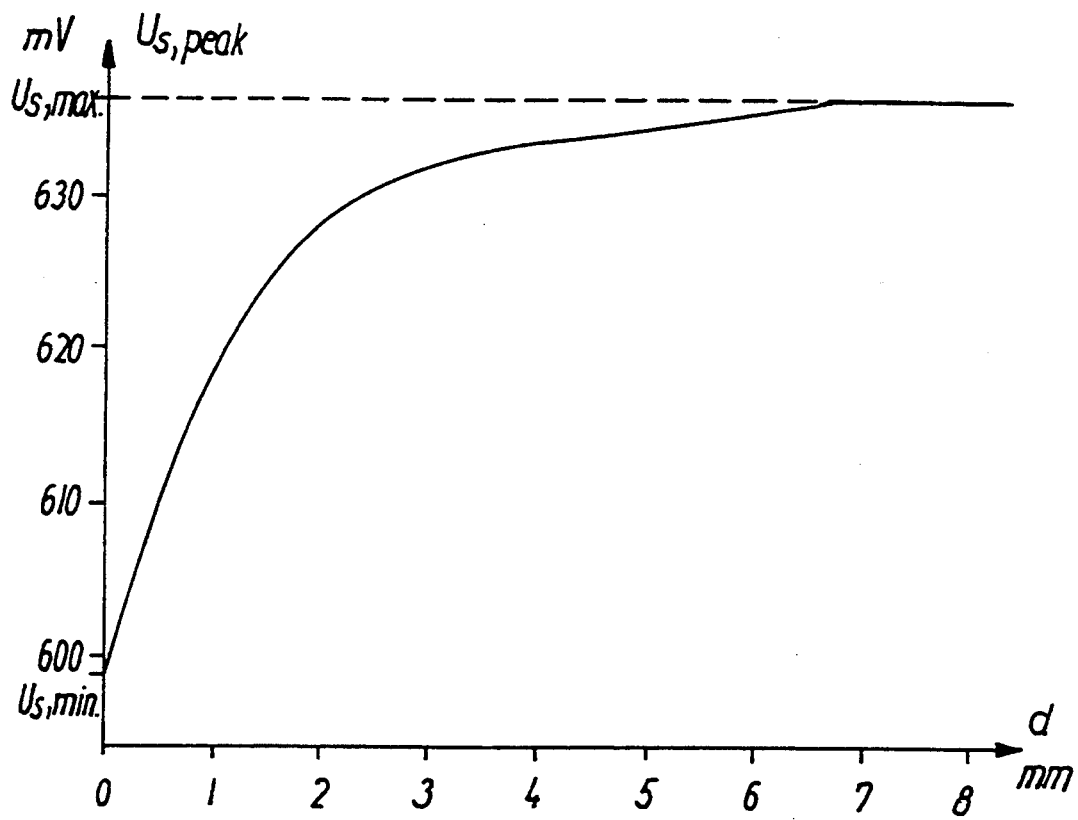
FIG. 8 is a curve showing how the peak value of the voltage across the coil circuit varies with the distance between the electrode and the calibration device.

In FIG. 8 is shown how the peak value $U_{s,peak}$ of the voltage across the coil circuit varies with the distance d between the surface 17 of the electrode housing 2 and the surface 34 of the upper flange 26a of the fixation ring 26. Across the coil circuit is applied the previously mentioned alternating voltage U with $U_{peak}=1$ V and frequency $f_u=150$ kHz. The curve has a minimum value $U_{s,min.}=598.7$ mV, corresponding to a position where the electrode 1 is fully inserted into the calibration device 20 and from here increases steeply until the distance d between the electrode 1 and the calibration device 20 is approx. 3 mm. Hereafter the curve flattens and approaches asymptotically the maximum value $U_{s,max}=635.8$ mV.

The steepness of the curve on the first part results in that the electrode 1 need not to be lifted very much from the calibration device 20 before the measured voltage $U_{s,peak}$ shows an unmistakably detectable change. As also seen from the drawing, it will also be unmistakably detectable whether the electrode 1 is lifted completely out of the calibration device 20, for example when the electrode 1 is to be used for measuring on a patient. There will, of course, be some uncertainty in the values $U_{s,min.}$ and $U_{s,max.}$, i.a. dependent on the tolerance of the coil 15 and of the accuracy of gluing of the silver body 3.

A first embodiment according to the invention comprises to detect in which position the electrode 1 is located. This is done by currently detecting the magnetic field in the coil circuit and comparing the detected signal with the predetermined signals for the positions of the electrode 1—in this case $U_{s,min.}$ (the electrode 1 in position for calibration) and $U_{s,max.}$ (the electrode 1 in position for measuring). As a result of the uncertainty mentioned above in these values, detected values within a certain range around $U_{s,min.}$ and $U_{s,max.}$, respectively will be accepted as representing these values.

When the connected monitor detects that the voltage $U_{s,peak}$ across the coil system lies within the range around $U_{s,min.}$, several functions are connected/disconnected, corresponding to the functions mentioned above in connection with calibration in the monitor system of the type TCM3 from Radiometer A/S. Moreover, it is only possible to activate a calibration when the voltage $U_{s,peak}$ lies within the range around $U_{s,min.}$. Hereby the risk of calibrating by mistake with the electrode 1 located on a patient is reduced, for example when measuring on a patient in an incubator.

When the electrode 1 has been removed from the calibration cup 22 and for example placed on a patient, the detected voltage $U_{s,peak}$ will lie within the range around $U_{s,max.}$. Now the electrode 1 is thermostated by means of the heating element 14, alarm functions, etc. are connected, and calibration can no longer be activated. With the voltage $U_{s,peak}$ in this range, the electrode 1 is adjusted for in vivo measurement.

Figure 9:
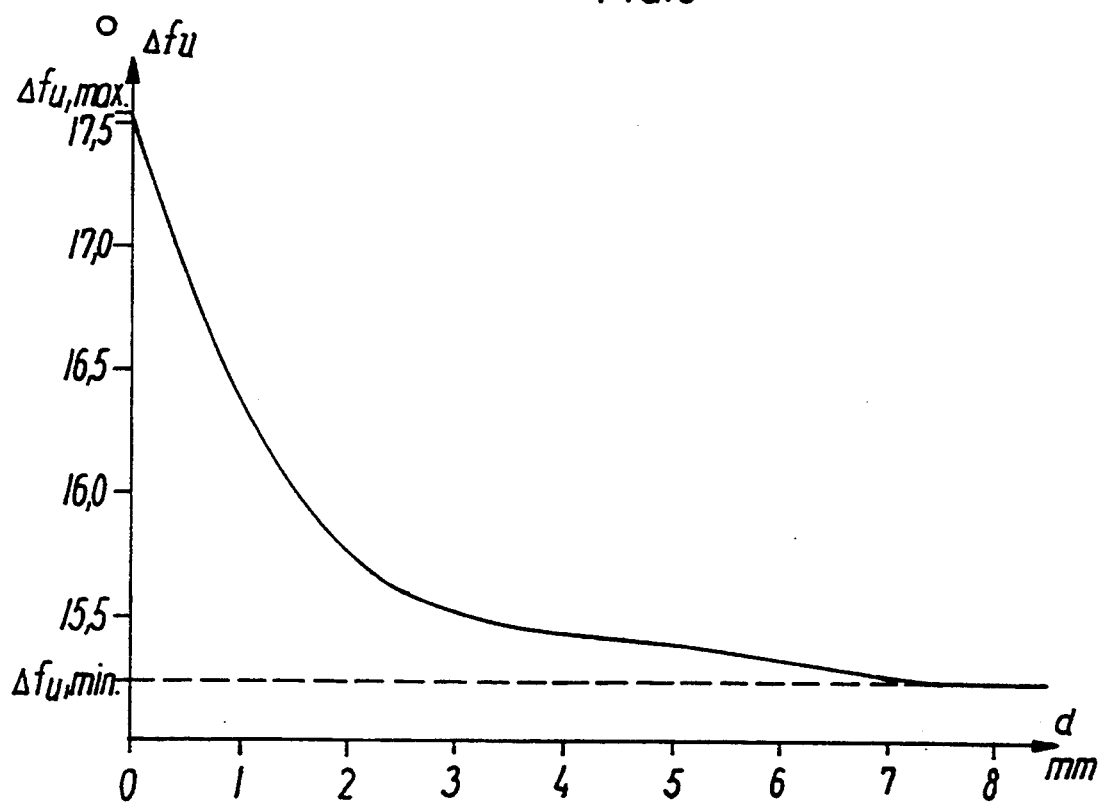
FIG. 9 is a curve showing how the phase of the voltage across the coil circuit is displaced in relation to the phase of the applied voltage when the distance between the electrode and the calibration device varies.

In FIG. 9 is shown how the phase shift $\Delta f_u$ of the voltage $U_s$ across the coil circuit varies with the distance d. The remarks in connection with FIG. 8 regarding the shape of the curve and the resulting possibilities of detection apply to this curve too, except that the curve for $\Delta f_u$ has a maximum $\Delta f_{u,max.}=17.5°$, where the curve for $U_{s,peak}$ has a minimum $U_{s,min.}$, and a minimum $\Delta f_{u,min.}=15.3°$, where the curve for $U_{s,peak}$ has a maximum $U_{s,max.}$.

If the electrode 1 is placed in a parking means 40, the ring 41 will—in a similar manner to the cup 22—influence the coil circuit so that the detected change in the voltage $U_{s,peak}$ or the phase shift $\Delta f_u$ no longer lies within the ranges around $U_{s,max.}$ or $\Delta f_{u,min.}$ (cf. FIG. 8). The ring 41 can be constructed in such a manner that it provides an equal detected signal for the voltage $U_{s,peak}$ or the phase shift $\Delta f_u$ as that of the cup 22. Hereby the functions mentioned in connection with calibration are connected/disconnected, said functions relating to a position where the electrode 1 is not applied for measuring. It is possible to activate calibration, but as the measured values for $pO_2$ and $pCO_2$ lie outside the range determined according to the calibration medium, the calibration will be rejected. Even if the parking means 40 has been located on a patient by mistake, the measured values for $O_2$ and $CO_2$ will represent the content of $O_2$ and $CO_2$ in the air, as the foil layer 42 is impermeable to these gasses.

Alternatively, the ring 41 on the parking means 40 may be constructed in such a manner that its influence on the coil circuit result in the detected signal for the voltage $U_{s,peak}$ or the phase shift $\Delta f_u$ will fall within a third range separated from the two others. The functions mentioned previously may also on this signal be connected/disconnected, but then it will not be possible to activate a calibration.

Metal objects other than the calibration cup 22 and the parking means ring 41 are also able to influence the coil circuit and cause a changed signal for the voltage $U_{s,peak}$ or the phase shift $\Delta f_u$. The coil 15 is, however, constructed and located in such a manner that only objects which penetrate into the groove 33 formed by the fixation ring 26 and the squeezing ring 28 (cf. FIG. 4) can cause a displacement of the detected signal for the magnetic field, corresponding to the electrode 1 being located in the calibration device 20 ($U_{s,min.}$, $\Delta f_{u,max.}$). For example, if the electrode 1 is placed on a metal surface, face, the detected signal will only be displaced to a value between the signal corresponding to an open-air position ($U_{s,max.}$, $\Delta f_{u,min.}$) and the signal corresponding to the calibration position ($U_{s,min.}$, $\Delta f_{u,max.}$). An external applied magnetic field may, however, influence the coil 15 too. In case that an external influence would cause calibration to be activated, when the electrode 1 is located in positions other than in the calibration device 20 and the parking means 40, the subsequent check on the measured values of $pO_2$ and $pCO_2$ will result in the calibration being rejected (cf. the above-mentioned description of the parking means 40).

In another embodiment it is not detected in which position the electrode 1 is located, but it is detected whether the electrode 1 changes its position. This is done by detecting the magnetic field in the coil circuit as mentioned above by measuring one of said parameters. When calibration is activated, a certain signal is detected. The monitor will not be adjusted for measuring on a patient until it detects that the measured signal changes more than a certain predetermined value and in a certain direction. The quantity and direction of this limit value is determined on the basis of the premeasured signals, when the electrode 1 is in measuring position (on a patient) and when the electrode 1 is in calibration position (in the calibration device 20), respectively. To safeguard against that a considerable unintended effect on the coil circuit is detected as a change of position, an alarm function will be activated if the detected change is considerably larger than the limit value.

For example, if the peak value $U_{s,peak}$ of the voltage across the coil circuit (see FIG. 8) is measured, the limit value is determined on the basis of $U_{s,max.}$ and $U_{s,min.}$. The sought quantity must be a little less than the difference between these and must therefore, as $U_{s,max.} - U_{s,min.} = 635.8$ mV $- 598.7$ mV $= 37.1$ mV, be approx. 35 mV. As $U_{s,measuring\ position} = U_{s,max.} > U_{s,calibration\ position} = U_{s,min.}$, the sign of the quantity must be positive. After activation and performance of calibration, the monitor will in this case not be adjusted for measuring on a patient until it detects that the signal for the peak value $U_{s,peak}$ of the voltage across the coil circuit detected at calibration is increased by approx. 35 mV.

Similarly, the monitor will, when it detects a decrease in the detected signal of approx. 35 mV, interpret this as if the electrode 1 has been transferred to a calibration device 20, and the functions mentioned previously in connection with calibration will be connected/disconnected.

If measuring on the phase shift $\Delta f_u$ instead of the peak value $U_{s,peak}$ of the alternating voltage U across the coil circuit, the sought limit value for the change is determined on the basis of $\Delta f_{u,min.}$ and $\Delta f_{u,max.}$. Thus, the limit value will be, as $\Delta f_{u,max.} - \Delta f_{u,min.} = 17.5 - 15.3 = 2.2°$, approx. 2.0°, and its sign will be negative, as $\Delta f_{u,measuring\ position} = \Delta f_{u,min.} < \Delta f_{u,calibration\ position} = \Delta f_{u,max.}$. Thus, after calibration the monitor is not adjusted for measuring until the detected signal for $\Delta f_u$ decreases by approx. 2.1°.

By use of this method it is possible to activate calibration of the electrode 1 with said electrode located in any position, but the monitor will only be adjusted for subsequent measuring if it detects a change of the measured signal of said quantity and direction. Thus, if calibration is performed with the electrode 1 located on a patient, measuring will not be performed on the patient. Displacement of the electrode 1 to a calibration device 20 will result in a change of the signal of a proper quantity, but the sign will indicate that the electrode 1 has been displaced from a measuring position to a calibration position and the performed calibration will be rejected.

The parking means 40 mentioned previously may, of course, be used by this method also. If the ring 41 on the parking means 40 is constructed in such a manner that it provides the same effect on the coil circuit of the electrode 1 as that of the calibration cup 22, the alarm functions, etc. mentioned previously will be connected/disconnected when removing the electrode 1 from a patient to the parking means. The ring 41 may, however, be constructed in such a manner that its influence on the coil circuit is different from that of the calibration cup 22. For example, if the signal from the influence of the ring 41 on the coil circuit is between the signals from the calibration cup 22 and the open air, then only the corresponding further limit values for the changes and the related directions need be entered to the monitor.

In the embodiment of FIG. 1 for the electrode 1 the coil 15 has the only function to form part of the circuit producing the magnetic field, with which the surroundings of the electrode 1 (the calibration cup 22, the ring 41) interact. The coil may, however, in another embodiment have more functions. For example, the coil may also act as a heating element for the electrode whereby the heating element mentioned in connection with FIG. 1 may be excluded.

The invention may, of course, be used for monitoring of the positions of other types of sensors as well. The only limitation is that a coil must be built into the sensor which is able to interact with the surroundings in the different positions in the manner as mentioned above.

We claim:

1. A method of monitoring the position of a sensor, the method comprising:
   providing a sensor comprising a coil integrated in a coil circuit, the coil generating a magnetic field in close proximity to the sensor;
   providing a mounting means adapted to engage with the sensor when the sensor is in a first position, the mounting means comprising a material for varying the magnetic field in the coil circuit when the sensor is in the first position;
   intermittently detecting the magnetic field in the coil circuit for detecting mutual induction between the coil circuit and the surroundings of the sensor; and
   determining from the magnetic field when the sensor is in the first position, or in a second position at which the sensor is not positioned adjacent to the mounting means.

2. The method according to claim 1, wherein the position of the sensor relative to the mounting means is determined by comparing the magnetic field in the coil circuit with predetermined signal ranges representing positions of the sensor relative to the mounting means.

3. The method according to claim 1, wherein a change of position of the sensor between the first and second positions is detected by the occurrence of a change in the detected signal for the magnetic field in the coil circuit, the change being greater than or equal to a certain predetermined quantity and having a given sign.

4. The method according to claim 1, wherein the magnetic field generated in the coil circuit is time-varying.

5. The method according to claim 1, wherein a change of the magnetic field in the coil circuit is detected as a change of the peak value of the voltage across the coil circuit.

6. The method according to claim 1, wherein a change of the magnetic field in the coil circuit is detected as a phase shift of the voltage across the coil circuit.

7. The method according to claim 1, wherein a change of the magnetic field in the coil circuit is detected as a change of the peak value of the current intensity through the coil circuit.

8. The method according to claim 1, wherein a change of the magnetic field in the coil circuit is detected as a phase shift of the current through the coil circuit.

9. The method according to claim 1, wherein the sensor is adapted to be connected to a monitor which is adapted to collect and process the signals for the magnetic field in the coil circuit.

10. The method according to claim 1 wherein the mounting means is a mounting ring on a calibration device.

11. The method according to claim 1 wherein the mounting means is a parking device.

12. The method according to claim 1 wherein the mounting means is a calibration device, and further comprising the steps of:
    providing a parking device adapted to engage with the sensor when the sensor is in a third position, the parking device comprising a material for varying the magnetic field in the coil circuit when the sensor is in the third position, the magnetic field in the third position being detectably different from the magnetic field in the first position; and
    determining from the magnetic field when the sensor is in the first position, in a second position at which the sensor is not positioned adjacent to the calibration device or the parking device, or in the third position.

13. A sensor positioning system which comprises:
    a sensor comprising a coil integrated in a coil circuit, the coil generating a magnetic field in close proximity to the sensor;
    mounting means adapted to engage with the sensor when the sensor is in a first position, the mounting means comprising a material for varying the magnetic field in the coil circuit when the sensor is in the first position;
    means for intermittently detecting the magnetic field in the coil circuit for detecting mutual induction between the coil circuit and the surroundings of the sensor; and
    means for determining from the magnetic field when the sensor is in the first position, or in a second position at which the sensor is not positioned adjacent to the mounting means.

14. The sensor positioning system according to claim 13 wherein the mounting means is a calibration device.

15. The sensor positioning system according to claim 14 wherein the calibration device comprises:
    a cup closed by a rupturable cover adapted to be ruptured by contact with the sensor, the cup comprising a calibration chamber containing a fluid suitable for calibration of the sensor;
    a membrane and membrane mounting means adapted to attach the membrane to the sensor as the sensor is placed into the calibration device; and
    fixation means adapted to fixedly engage with the sensor.

16. The sensor positioning system according to claim 13 wherein the mounting means is a parking device for parking the sensor.

17. The sensor positioning system according to claim 16 wherein the parking device comprises:
    a ring of an electrically conductive material shaped to correspond to the shape of the sensor, the ring being attached to a foil having adhesive on the surface of the foil opposite the ring, the foil adapted to be placed on a surface with the adhesive in contact with the surface, the ring being constructed of a material adapted so that mutual induction between the coil circuit of the sensor and the ring occurs with the sensor in the first position.

18. The sensor positioning system according to claim 13 wherein the mounting means is a calibration device, and further comprising:
    a parking device adapted to engage with the sensor when the sensor is in a third position, the parking device comprising a material for varying the magnetic field in the coil circuit when the sensor is in the third position, the magnetic field in the third position being detectably different from the magnetic field in the first position; and
    means for determining from the magnetic field when the sensor is in the first position, in a second position at which the sensor is not positioned adjacent to the calibration device or the parking device, or in the third position.

* * * * *